United States Patent
Sakuma et al.

(10) Patent No.: US 9,689,834 B2
(45) Date of Patent: Jun. 27, 2017

(54) GAS SENSOR

(71) Applicant: NGK SPARK PLUG CO., LTD., Nagoya-shi, Aichi (JP)

(72) Inventors: Shun Sakuma, Kakamigahara (JP); Shigeki Mori, Seki (JP); Masaki Mizutani, Aichi-ken (JP); Yuichi Yamada, Komaki (JP); Shohei Yoshiyasu, Komaki (JP); Hirotaka Tsukamatsu, Nagoya (JP); Makoto Shimoide, Aichi-ken (JP)

(73) Assignee: NGK SPARK PLUG CO., LTD., Aichi (JP)

( * ) Notice: Subject to any disclaimer, the term of this patent is extended or adjusted under 35 U.S.C. 154(b) by 839 days.

(21) Appl. No.: 13/629,516

(22) Filed: Sep. 27, 2012

(65) Prior Publication Data
US 2013/0074582 A1    Mar. 28, 2013

(30) Foreign Application Priority Data

Sep. 27, 2011 (JP) ................................. 2011-211327
Aug. 10, 2012 (JP) ................................. 2012-178373

(51) Int. Cl.
*G01N 7/00* (2006.01)
*G01N 27/407* (2006.01)
*G01N 33/00* (2006.01)

(52) U.S. Cl.
CPC ..... *G01N 27/4077* (2013.01); *G01N 27/4071* (2013.01); *G01N 33/004* (2013.01); *G01N 33/0037* (2013.01)

(58) Field of Classification Search
CPC .... H05B 3/28; A61F 7/007; A61F 2007/0001; G01N 27/4071; G01N 27/406; G01N 27/26

(Continued)

(56) References Cited

U.S. PATENT DOCUMENTS 5,556,526 A * 9/1996 Fukaya ................ G01N 27/407
                                                                174/167
6,645,360 B1 * 11/2003 Eisele ................ G01N 27/4077
                                                                204/408

(Continued)

FOREIGN PATENT DOCUMENTS

JP          60-9192 A      1/1985
JP          62-80366 U     5/1987
(Continued)

OTHER PUBLICATIONS

Communication dated Jul. 15, 2014, issued by the Japanese Patent Office in corresponding Application No. 2012-178373.

*Primary Examiner* — Robert R Raevis
*Assistant Examiner* — Gedeon M Kidanu
(74) *Attorney, Agent, or Firm* — Sughrue Mion, PLLC

(57) ABSTRACT

A gas sensor including a plate-shaped detecting element is disclosed, wherein the detecting element has a pair of principle surfaces and a pair of side surfaces adjacent to the pair of principle surfaces, in a radical direction thereof, wherein a first chamfered portion is provided between at least one first principal surface of the pair of principal surfaces and the rear end surface of the detecting element, and wherein the angle between a first axis ridgeline portion formed by the first principal surface and a first side surface that is one of the pair of side surfaces and extending in the direction of the axis, and a first width ridgeline formed by the first principal surface and the first chamfered portion and extending in a width direction is larger than 90°.

6 Claims, 11 Drawing Sheets

(58) Field of Classification Search
USPC .............. 73/23, 31; 204/424, 426, 429, 431; 422/83
See application file for complete search history.

(56) References Cited

U.S. PATENT DOCUMENTS

| | | | | |
|---|---|---|---|---|
| 8,168,053 | B2* | 5/2012 | Kobayashi ......... | G01N 27/4071 204/424 |
| 2003/0074950 | A1 | 4/2003 | Yamada et al. | |
| 2006/0220159 | A1* | 10/2006 | Matsuo .............. | G01N 27/4062 257/414 |
| 2008/0067067 | A1* | 3/2008 | Oya .................... | G01N 27/419 204/426 |
| 2008/0202205 | A1* | 8/2008 | Suzuki et al. ............... | 73/23.21 |
| 2008/0302661 | A1* | 12/2008 | Suzuki ............... | G01N 27/4073 204/424 |
| 2009/0117007 | A1* | 5/2009 | Furuta ................ | G01N 27/4071 422/83 |

FOREIGN PATENT DOCUMENTS

| | | |
|---|---|---|
| JP | 2-62756 U | 5/1990 |
| JP | 2001-188060 A | 7/2001 |
| JP | 2006-170862 A | 6/2006 |
| JP | 2006-300923 A | 11/2006 |
| JP | 2007-163272 A | 6/2007 |
| JP | 2008-102130 A | 5/2008 |

* cited by examiner

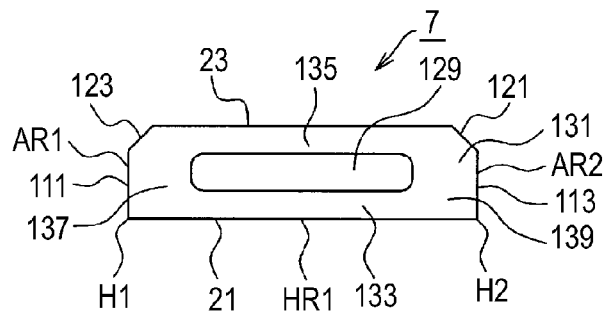
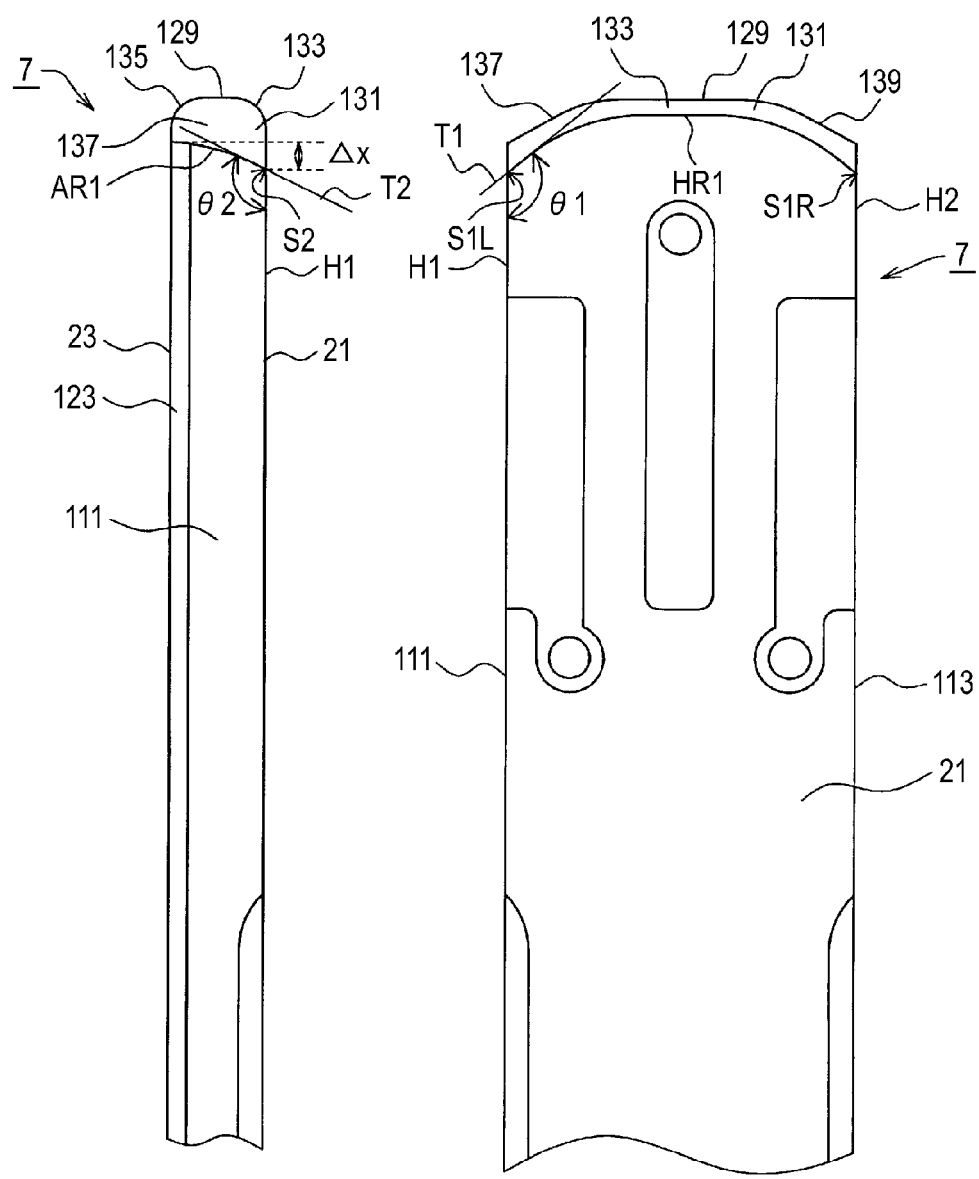

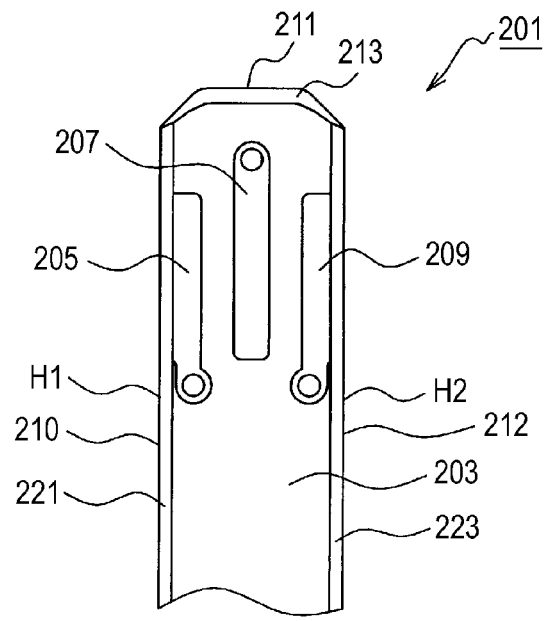
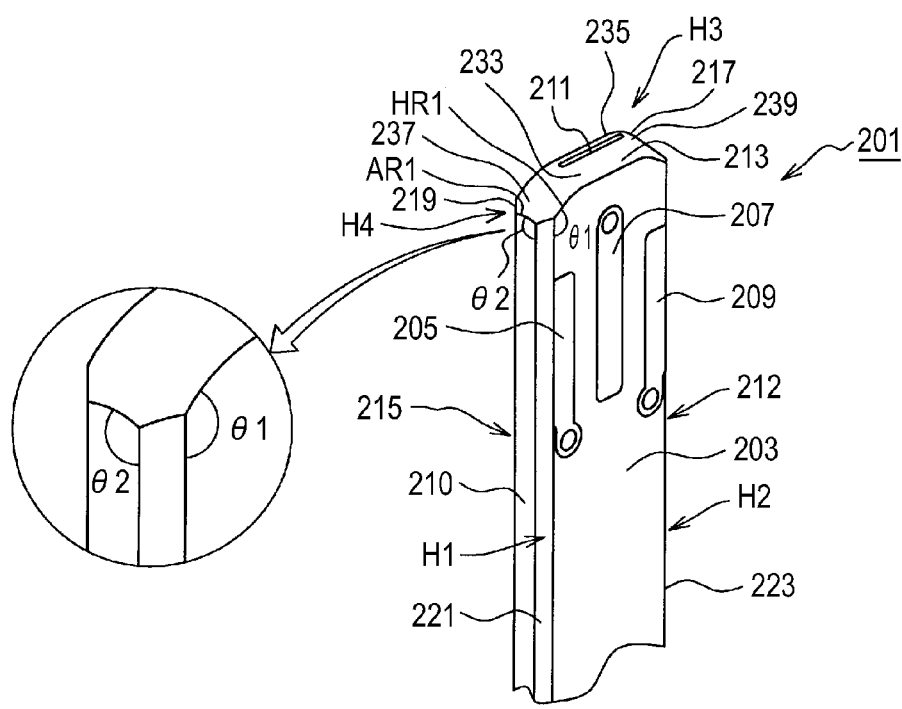

GAS SENSOR

BACKGROUND OF THE INVENTION

Field of the Invention

The present invention relates to a gas sensor including a detecting element for detecting a specific gas contained in an object measurement gas.

Description of the Related Art

In the related art, for example, gas sensors including a detecting element for detecting a specific gas, such as oxygen, which is contained in an object measurement gas, such as exhaust gas, are widely known.

In this type of gas sensor, in addition to the detecting element, a metal shell that allows a front end portion and a rear end portion of the detecting element to protrude therefrom and surrounds the periphery of the detecting element, a terminal metal fixture that abuts onto the rear end portion of the detecting element, and a tubular separator with insulating properties that accommodates the rear end portion of the detecting element or the terminal metal fixture, and the like are provided.

Among these, for example, a plate-shaped laminated type oxygen sensor element in which a plurality of ceramic layers or the like are laminated is known, as the detecting element, as described in JP-A-2007-163272. In detail, this detecting element includes a detecting portion or a heater at a front end portion exposed to an object measurement gas, such as exhaust gas. Further, electrode pads are connected to lead wires that extend from the detecting portion or the heater, on the outer surface of the rear end portion, and the terminal metal fixture is adapted to abut the electrode pads.

Incidentally, in the above-described related art, as shown in FIG. 11A, C chamfering is performed on a rear end portion P2 of a detecting element P1 to provide a C chamfered portion P3. This is because, when the rear end portion P2 of the plate-shaped detecting element P1 is inserted into a separator P5 (refer to FIG. 11B), the C chamfered portion P3 is easily inserted to follow a through hole P6 of the separator P5. Further, there is a possibility that a corner portion P7 of the rear end portion P2 may come into contact with an opening of the through hole P6 of the separator P5. Further, chipping may occur at the corner portion P7 of the rear end portion P2 of the detecting element P1.

In addition, the corner portion P7 is a portion where a ridgeline P11 formed by a principal surface P8 and a side surface P9, a ridgeline P12 formed by the principal surface P8 and a rear end surface P10, and a ridgeline P13 formed by a side surface P9 and the rear end surface P10 are combined.

However, in a case where a gas sensor is manufactured, as shown in FIG. 11B, the detecting element P1 is inserted at an incline with respect to the separator P5 and not coaxially with the separator P5. In that case, there is a problem in that a corner portion P14 of the rear end portion P2 of the detecting element P1 may strike the opening of the through hole P6 of the separator P5 or the inner surface of the separator P5, and chipping may occur in the detecting element P1.

In addition, the corner portion P14 is a portion where the ridgeline P11 formed by the principal surface P8 and the side surface P9, a ridgeline P15 formed by the principal surface P8 and the C chamfered portion P3, and a ridgeline P16 formed by the side surface P9 and the C chamfered portion P3 are combined.

That is, even if the rear end portion P2 of the detecting element P1 is provided with the C chamfered portion P3 in order to improve the insertion performance of the detecting element P1 into the separator P5 and prevent chipping of the corner portion P7, there is a problem in that the occurrence of chipping in the corner portion P14 of the detecting element P1 cannot be sufficiently suppressed by providing the C chamfered portion P3 alone.

SUMMARY OF THE INVENTION

The invention has been made in order to solve the above problems, and an object thereof is to provide a gas sensor that can prevent the occurrence of chipping in a rear end portion of a detecting element.

(1) The invention provides, in a first aspect, a gas sensor including a plate-shaped detecting element that extends in the direction of an axis and has a front end portion directed at an object measurement gas; a metal shell surrounding a periphery of the detecting element such that a front end portion and a rear end portion of the detecting element protrude therefrom; and a tubular member that accommodates the rear end portion of the detecting element. The detecting element has a pair of principal surfaces and a pair of side surfaces adjacent to the pair of principal surfaces, in a radial direction thereof. A first chamfered portion is provided between at least one first principal surface of the pair of principal surfaces and the rear end surface of the detecting element. The angle between a first axis ridgeline portion formed by the first principal surface and a first side surface that is one of the pair of side surfaces and extending in the direction of the axis, and a first width ridgeline formed by the first principal surface and the first chamfered portion and extending in a width direction is larger than 90°.

The rear end portion of the detecting element of the invention includes the first chamfered portion between the first principal surface and the rear end surface, and the angle between the first axis ridgeline portion formed by the first principal surface and one first side surface and extending in the direction of the axis, and the first width ridgeline formed by the first principal surface and the first chamfered portion and extending in the width direction is set to be larger than 90°.

Thereby, the first width ridgeline is provided closer to the rear end side than the corner portion where the first axis ridgeline portion and the first width ridgeline are combined. Hence, when the rear end portion of the detecting element is inserted into the tubular member, even if the detecting element is inserted at an incline with respect to the tubular member and not coaxially with the tubular member, the opening or inner surface of the tubular member comes into contact with the first width ridgeline. Thereby, the corner portion of the detecting element does not readily come into contact with the opening or inner surface of the tubular member. As a result, chipping can be avoided.

Moreover, the corner portion where the first axis ridgeline portion and the first width ridgeline are combined becomes smoother by the angle between the first axis ridgeline portion and the first width ridgeline being set so as to be larger than 90°. As a result, when the rear end portion of the detecting element is inserted into the tubular member, even if the detecting element is inserted at an incline with respect to the tubular member and not coaxially with the tubular member, and the corner portion of the detecting element strikes the opening or inner surface of the tubular member, chipping does not easily occur.

Moreover, since the first chamfered portion is provided between the first principal surface and the rear end surface, when the rear end portion of the plate-shaped detecting element is inserted into the tubular member, the first chamfered portion is easily inserted to follow the through hole of the tubular member.

In addition, the detecting element has a plate shape in which a pair of principal surfaces and a pair of side surfaces are adjacent to each other in the radial direction thereof. Two facing surfaces among four surfaces arranged in the radial direction of the detecting element may be regarded as the principal surfaces, and two surfaces adjacent to the principal surfaces may be regarded as the side surfaces.

Moreover, the first width ridgeline may have a straight line or may have a curved line. In addition, in a case where the first width ridgeline has a curved line, the "angle between the first axis ridgeline portion and the first width ridgeline" is taken as the angle between (i) the tangential line of the first width ridgeline at the corner portion where the first axis ridgeline portion and the first width ridgeline are combined, and (ii) the first axis ridgeline portion. Additionally, the first width ridgeline may have a straight line in the width direction, and the straight line may bend in the middle. In addition, in a case where the first width ridgeline has a straight line that is bent in the middle, the "angle between the first axis ridgeline portion and the first width ridgeline" is taken as the angle between (i) the straight line of the first width ridgeline connected to the corner portion where the first axis ridgeline portion and the first width ridgeline are combined, and (ii) the first axis ridgeline portion.

Additionally, the first principal surface and the first side surface of the detecting element may be adjacent via a first axis ridgeline formed by the first principal surface and the first side surface and extending in the direction of the axis, or may be adjacent via a first long side chamfered portion provided by the first principal surface and the first side surface and extending in the direction of the axis. In addition, when the detecting element is provided with the long side chamfered portion, the long side chamfered portion is taken as the first axis ridgeline portion, and the "angle between the first axis ridgeline portion and the first width ridgeline" is taken as the angle between the long side chamfered portion (more specifically, an axis ridgeline formed by the long side chamfered portion and the first principal surface), and the first width ridgeline.

(2) In a preferred embodiment of the gas sensor (1) above, the angle between (i) a second axis ridgeline portion formed by the first principal surface and a second side surface different from the first side surface of the pair of side surfaces and extending in the direction of the axis, and (ii) the first width ridgeline is larger than 90°.

The first width ridgeline is provided closer to the rear end side than the corner portion where the second axis ridgeline portion and the first width ridgeline are combined by setting the angle between the second axis ridgeline portion and the first width ridgeline to be larger than 90°. Thereby, when the rear end portion of the detecting element is inserted into the tubular member, even if the detecting element is inserted at an incline with respect to the tubular member and not coaxially with the tubular member, the opening or inner surface of the tubular member comes into contact with the first width ridgeline. As a result, the corner portion of the detecting element does not easily come into contact with the opening or inner surface of the tubular member and chipping can be avoided.

Moreover, the corner portion where the second axis ridgeline portion and the first width ridgeline are combined becomes smoother by setting the angle between the second axis ridgeline portion and the first width ridgeline to be larger than 90°. As a result, when the rear end portion of the detecting element is inserted into the tubular member, even if the detecting element is inserted at an incline with respect to the tubular member and not coaxially with the tubular member, and the corner portion of the detecting element strikes the opening or inner surface of the tubular member, chipping does not easily occur.

In addition, in a case where the first width ridgeline has a curved line, the "angle between the second axis ridgeline portion and the first width ridgeline" is taken as the angle between (i) the tangential line of the first width ridgeline at the corner portion where the second axis ridgeline portion and the first width ridgeline are combined, and (ii) the second axis ridgeline portion. Additionally, in a case where the first width ridgeline has a straight line that is bent in the middle, the "angle between the second axis ridgeline portion and the first width ridgeline" is taken as the angle between (i) the straight line of the first width ridgeline connected to the corner portion where the second axis ridgeline portion and the first width ridgeline are combined, and (ii) the second axis ridgeline portion.

Additionally, the first principal surface and the second side surface of the detecting element may be adjacent via a second axis ridgeline formed by the first principal surface and the second side surface and extending in the direction of the axis, or may be adjacent via a long side chamfered portion provided by the first principal surface and the second side surface and extending in the direction of the axis. In addition, when the detecting element is provided with the long side chamfered portion, the long side chamfered portion is taken as the second axis ridgeline portion, and the "angle between the second axis ridgeline portion and the first width ridgeline" is taken as the angle between (i) the long side chamfered portion (more specifically, an axis ridgeline formed by the long side chamfered portion and the first principal surface), and (ii) the first width ridgeline.

(3) In a preferred embodiment of the gas sensor (2) above, the first width ridgeline has a circular-arc shape in which a central portion thereof in the width direction protrudes to a rear end side.

Since the first width ridgeline has a circular-arc shape in which a central portion thereof in the width direction protrudes to a rear end side, when the rear end portion of the detecting element is inserted into the tubular member, the central portion of the detecting element abuts in a case where the opening or inner surface of the tubular member comes into contact with the first width ridgeline. As a result, the corner portion of the detecting element does not easily come into contact with the opening or inner surface of the tubular member, and consequently, chipping can be avoided.

(4) In a preferred embodiment of the gas sensor of any one of (1) to (3) above, a second chamfered portion is provided between (i) the first side surface and the rear end surface, and the angle between a first thickness ridgeline formed by the first side surface and the second chamfered portion and extending in the thickness direction of the detecting element, and (ii) the first axis ridgeline portion is larger than 90°.

In the gas sensor (4) above, in the first side surface of the detecting element, the angle between the first axis ridgeline portion and the first thickness ridgeline is set so as to be larger than 90°. Thereby, the first thickness ridgeline is provided closer to the rear end side than the corner portion where the first axis ridgeline portion and the first thickness ridgeline are combined. Hence, when the rear end portion of the detecting element is inserted into the tubular member, even if the detecting element is inserted at an incline with respect to the tubular member and not coaxially with the tubular member, the opening or inner surface of the tubular member comes into contact with the first thickness ridgeline. As a result, the corner portion of the detecting element does not easily come into contact with the opening or inner surface of the tubular member and chipping can be avoided.

Moreover, the corner portion where the first axis ridgeline portion and the first thickness ridgeline are combined and become smoother by setting the angle between the first axis ridgeline portion and the first thickness ridgeline so as to be larger than 90°. As a result, when the rear end portion of the detecting element is inserted into the tubular member, even if the detecting element is inserted at an incline with respect to the tubular member and not coaxially with the tubular member, and the corner portion of the detecting element strikes the opening or inner surface of the tubular member, chipping does not easily occur.

Moreover, since the second chamfered portion is provided between the first side surface and the rear end surface, when the rear end portion of the plate-shaped detecting element is inserted into the tubular member, the second chamfered portion is easily inserted to follow the through hole of the tubular member.

Moreover, the first thickness ridgeline may have a straight line or may have a curved line. In addition, in a case where the first thickness ridgeline has a curved line, the "angle between the first axis ridgeline and the first thickness ridgeline" is taken as the angle between (i) the tangential line of the first thickness ridgeline at the corner portion where the first axis ridgeline and the first thickness ridgeline are combined, and (ii) the first axis ridgeline. Additionally, the first thickness ridgeline may have a straight line in the width direction, and the straight line may bend in the middle. In addition, in a case where the first thickness ridgeline has a straight line that is bent in the middle, the "angle between the first axis ridgeline and the first thickness ridgeline" is taken as the angle between (i) the straight line of the first thickness ridgeline connected to the corner portion where the first axis ridgeline and the first thickness ridgeline are combined, and (ii) the first axis ridgeline.

Additionally, the detecting element may be adjacent via the first axis ridgeline formed by the first principal surface and the first side surface and extending in the direction of the axis, or may be adjacent via the long side chamfered portion provided by the first principal surface and the first side surface and extending in the direction of the axis. In addition, when the detecting element is provided with the long side chamfered portion, the long side chamfered portion is taken as the first axis ridgeline portion, and the "angle between the first axis ridgeline portion and the first thickness ridgeline" is taken as the angle between (i) the long side chamfered portion (more specifically, an axis ridgeline formed by the long side chamfered portion and the first side surface), and (ii) the first width ridgeline.

(5) In another preferred embodiment of the gas sensor of any one of (1) to (4) above, the gas sensor further comprises a second axis ridgeline portion formed by the first principal surface and a second side surface different from the first side surface of the pair of side surfaces and extending in the direction of the axis, wherein a plurality of electrode pads is provided on the first principal surface, wherein and two electrode pads among the plurality of electrode pads are provided side by side along the width direction on the first principal surface of the detecting element so as to be adjacent to the first axis ridgeline portion and the second axis ridgeline portion, and wherein a value obtained by dividing a total value of the width dimensions of the two electrode pads by the width dimension of the first principal surface is 0.4 or less.

In the gas sensor (5) above, the total value of the width dimensions of the two electrode pads that are adjacent to the first axis ridgeline portion and the second axis ridgeline portion to the value of the width dimension of the first principal surface is 40% or less.

First of all, when the rear end portion of the detecting element is inserted into the tubular member, the first axis ridgeline portion, the second axis ridgeline portion, and the like along the direction of the axis of the detecting element easily come into contact with the inner surface of the tubular member in a case where the detecting element is inserted at an incline with respect to the tubular member and not coaxially with the tubular member. Therefore, it is preferable to provide a chamfered portion. However, as described above, in a case where the width dimensions of the two electrode pads are small, it is dimensionally difficult to perform chamfering on the rear end portion (that is all the axis ridgeline portions of the detecting element from the front end side to the rear end side thereof) on the respective sides of the detecting element in the direction of the axis. In contrast, chamfering is performed on the rear end portion of the detecting element so as to have the above-described predetermined angle as in this embodiment. Thereby, chipping can be suppressed even if chamfering is not performed on the axis ridgeline portion in the direction of the axis.

In addition, the "total value of the width dimensions of the two electrode pads" indicates the total value of the width dimensions of the electrode pads (connected to the first axis ridgeline portion and the second axis ridgeline portion) that are adjacent to the first axis ridgeline portion and the second axis ridgeline portion.

(6) In yet another preferred embodiment of the gas sensor of any one of (1) to (6) above, a third chamfered portion is provided between (i) a second principal surface different from the first principal surface of the pair of principal surfaces, and (ii) the rear end surface of the detecting element, and a long side chamfered portion is provided by the second principal surface and the first side surface so as to be connected to the third chamfered portion. Further, a chamfering length in the direction of the axis of the first chamfered portion is larger than the chamfering length in the direction of the axis of the third chamfered portion.

In the gas sensor (6) above, the chamfering length of the first chamfered portion in the direction of the axis is set to be larger than the chamfering length of the third chamfered portion in the direction of the axis.

In a case where the long side chamfered portion provided by the second principal surface and the first side surface is connected to the third chamfered portion that faces the first chamfered portion, the corner portion formed by the long side chamfered portion, the third chamfered portion, the second principal surface, and the first side surface become smoother, and consequently, chipping can be avoided at the corner portion. In contrast, even if the long side chamfered portion is not connected to the first chamfered portion, the corner portion formed by the first principal surface, the first side surface, and the first chamfered portion also become sufficiently smooth by setting the chamfering length as specified in this embodiment. As a result, chipping can be prevented from easily occurring at the corner portion.

In addition, in a case where the first chamfered portion and the second chamfered portion have different chamfering lengths in the width direction, a comparison is made by the greatest chamfering length.

BRIEF DESCRIPTION OF THE DRAWINGS

FIG. 7A is a plan view showing the rear end portion of the detecting element, FIG. 7B is a front view showing the rear end portion of the detecting element, and FIG. 7C is a side view showing the rear end portion of the detecting element;

FIG. 8A is a front view showing a rear end portion of a detecting element of a second embodiment, and FIG. 8B is a perspective view showing the rear end portion of the detecting element;

DETAILED DESCRIPTION OF THE INVENTION

Embodiments of the invention will be described below with reference to the drawings. However, the present invention should not be construed as being limited thereto.

In addition, in the respective embodiments shown below, a full-range air-fuel ratio sensor (hereinafter simply referred to as an air-fuel ratio sensor) that is a kind of gas sensor, specifically, an air-fuel ratio sensor, to which a detecting element (gas sensor element) that detects a specific gas (oxygen) in exhaust gas serving as an object measurement gas is assembled for feed-back control of an air-fuel ratio in automobiles or various internal combustion engines and is mounted on an exhaust pipe of an internal combustion engine, will be described as an example.

First Embodiment a) The configuration of an overall air-fuel ratio sensor of the present embodiment will first be described.

Figure 1:
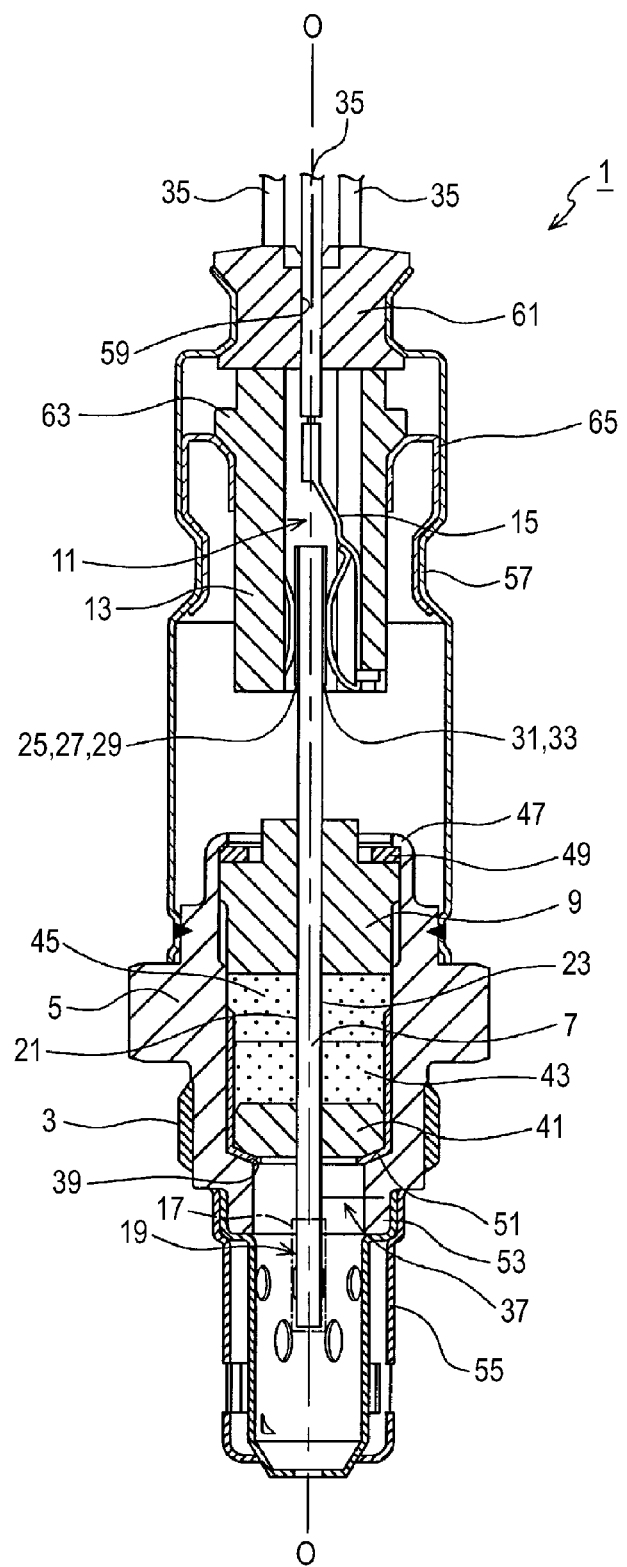
FIG. 1 is an explanatory view showing a state where an air-fuel ratio sensor of a first embodiment is fractured along the axial direction.

As shown in FIG. 1, the air-fuel ratio sensor 1 of the present embodiment includes a tubular metal shell 5 that has a threaded portion 3, for fixing to an exhaust pipe, formed in an outer surface thereof, a plate-shaped detecting element 7 that extends in the direction of an axis O, a tubular ceramic sleeve 9 that is arranged so as to surround the radial periphery of the detecting element 7, a tubular insulated contact member (hereinafter also referred to as a separator) 13 that is arranged in a state where the inner surface of a through hole 11 that passes through in the direction of the axis surrounds the periphery of a rear end portion of the detecting element 7, and five connecting terminals (only two terminals are shown in FIG. 1) 15 that are arranged between the detecting element 7 and the separator 13.

In the detecting element 7, as described in detail below, a detecting portion 19 covered with a porous layer 17 is formed on the front end side (lower side in FIG. 1: a front end portion in the direction of the axis O) directed to the gas serving as an object measurement gas, and electrode pads 25, 27, 29, 31 and 33 (refer to FIG. 4) are formed on a first principal surface 21 and a second principal surface 23 that have a positional relationship of the front and back in the outer surface on the rear end side (upper side in FIG. 1: a rear end portion in the direction of the axis O).

The connecting terminals 15 are arranged between the detecting element 7 and the separator 13, and are electrically connected to the electrode pads 25 to 33 of the detecting element 7, respectively. Additionally, the connecting terminals 15 are also electrically connected to lead wires 35 disposed inside the sensor from the outside, and form current paths for electric currents that flow between an external instrument to which the lead wires 35 are connected, and the electrode pads 25 to 33.

The metal shell 5 has a through hole 37 that passes through in the direction of the axis, and is formed in a substantially tubular shape having a shoulder portion 39 that protrudes radially inward of the through hole 37. The metal shell 5 is adapted to hold the detecting element 7 inserted through the through hole 37 in a state where the detecting portion 19 is arranged on the outside of the front end of the through hole 37 and the electrode pads 25 to 33 are arranged on the outside of the rear end of the through hole 37.

Additionally, an annular ceramic holder 41, talc rings 43 and 45, and the above-described ceramic sleeve 9 are laminated in this order from the front end side to the rear end side inside the through hole 37 of the metal shell 5 in the state of surrounding the radial periphery of the detecting element 7.

A crimping packing 49 is arranged between the ceramic sleeve 9 and a rear end portion 47 of the metal shell 5, and a metal holder 51 for holding the talc ring 43 and the ceramic holder 41 is arranged between the ceramic holder 41 and the shelf portion 39 of the metal shell 5. In addition, the rear end portion 47 of the metal shell 5 is crimped so as to push the ceramic sleeve 9 against the front end side via the crimping packing 49.

Moreover, a protector 55 adapted to have a double structure made of metal (for example, stainless steel or the like) that covers a protruding portion of the detecting element 7 is attached to an outer periphery of a front end portion 53 of the metal shell 5 by welding or the like.

On the other hand, an external cylinder 57 is fixed to an outer periphery of the metal shell 5 on the rear end side. Additionally, a grommet 61 formed with a lead wire insertion through hole 59 through which five lead wires 35 (three are shown in FIG. 1) electrically connected to the electrode pads 25 to 33 respectively, are inserted, is arranged at an opening portion of the external cylinder 57 on the rear end side.

In addition, the separator 13 is formed with a protruding portion 63, and the protruding portion 63 is fixed to the external cylinder 57 via a holding member 65.

Figure 2:
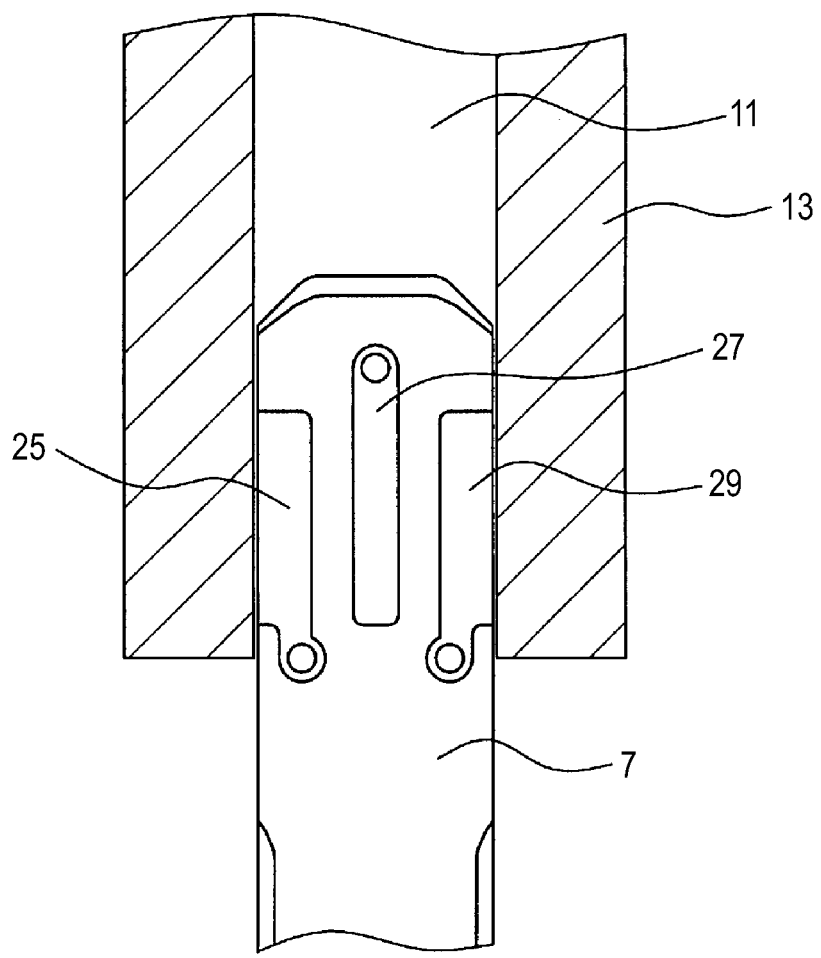
FIG. 2 is an explanatory view showing a state where a rear end portion of a detecting element is inserted into the inside of a separator, in an enlarged manner.

As shown in FIG. 2, the rear end portion of the detecting element 7 protruding from the rear end portion 47 of the metal shell 5 is arranged within the through hole 11 of the separator 13. In addition, the separator 13 is arranged so as to cover the periphery of the electrode pads 25 to 33 formed on the surface of the detecting element 7 on the rear end side.

b) Next, the configuration of the detecting element 7 that is a main part of the present embodiment will be described in detail.

Figure 3:
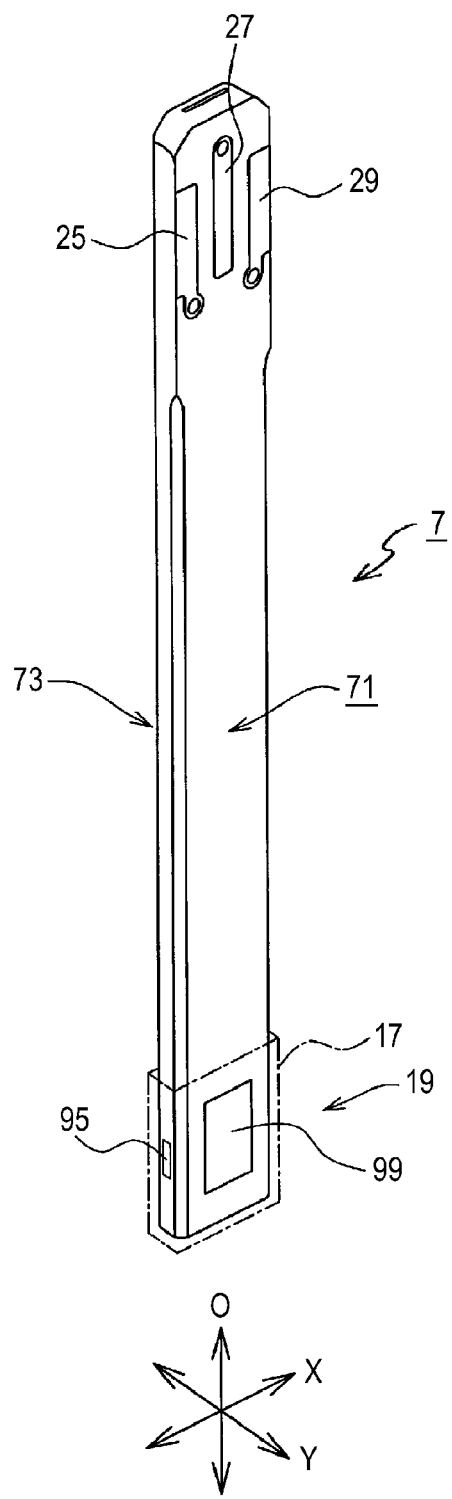
FIG. 3 is a perspective view showing the detecting element.

As shown in FIG. 3, the detecting element 7 is a long plate material that extends in the direction of the axis. In addition, description will be made below, with the width direction of the detecting element 7 shown in FIG. 3 as an X-axis direction and the thickness direction of the detecting element shown in FIG. 3 as a Y-axis direction.

The detecting element 7 is an element in which a plate-shaped element portion 71 that is arranged on one side (front side that is the near side of FIG. 3) in the thickness direction and extends in the direction of the axis O, and a plate-shaped heater 73 that is arranged on the opposite side (back side) of the element portion 71 and similarly extends in the direction of the axis O are laminated.

Figure 4:
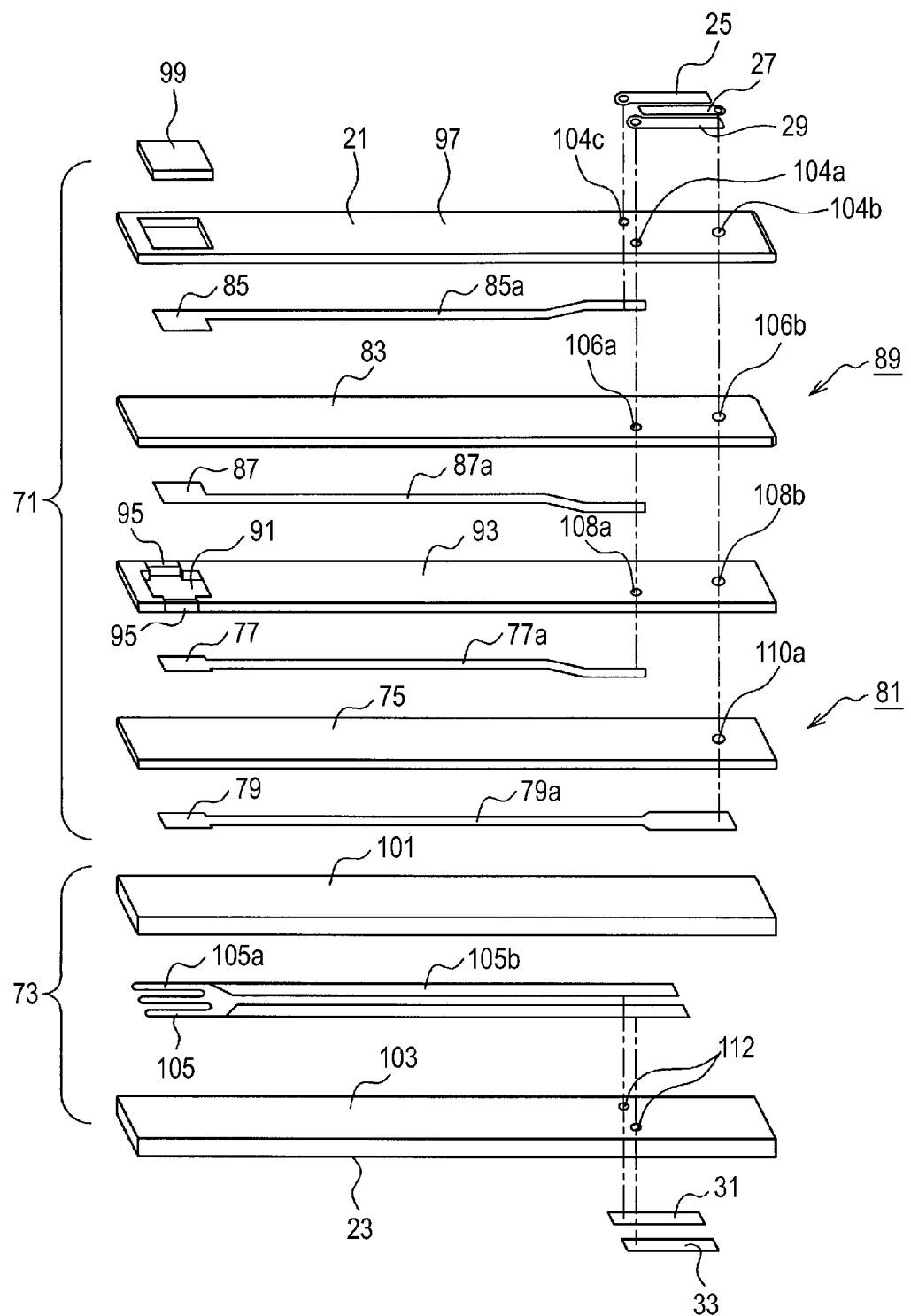
FIG. 4 is a perspective view showing the detecting element in a disassembled manner.

Among these, the element portion 71, as shown in an exploded manner in FIG. 4, is constituted by an oxygen concentration cell 81 in which porous electrodes 77 and 79 are arranged on both sides of a solid electrolyte substrate 75, similarly an oxygen pump cell 89 in which the porous electrodes 85 and 87 are arranged on both sides of a solid electrolyte substrate 83, and a spacer 93 that is laminated between both the cells 81 and 89 to form a hollow measurement gas chamber (gas detector chamber) 91, and the like.

In the oxygen concentration cell 81, the porous electrodes 77 and 79 are arranged in the thickness direction (upper and lower surfaces of FIG. 4) with the solid electrolyte substrate 75 interposed therebetween. Among these, the porous electrode 77 is arranged so as to be exposed to the gas detector chamber 91, and has a lead portion 77a, which extends in the direction of the axis O, connected thereto. On the other hand, the porous electrode 79 is arranged so as to face the porous electrode 77, and has a lead portion 79a, which extends in the direction of the axis O, connected thereto. The solid electrolyte substrate 75 is formed from zirconia in which yttria is contained in the form of a solid solution as a stabilizing agent, and the porous electrodes 77 and 79 and the lead portions 77a and 79a are formed mainly of Pt.

In the oxygen pump cell 89, the porous electrodes 85 and 87 are arranged in the thickness direction (upper and lower surfaces of FIG. 4) with the solid electrolyte substrate 83 interposed therebetween. On the other hand, the porous electrode 87 is arranged so as to be exposed to the gas detector chamber 91, and has a lead line 87a, which extends in the direction of the axis O, connected thereto. In addition, this allows the porous electrode 77 and the porous electrode 87 to face each other. On the other hand, the porous electrode 85 is arranged so as to face the porous electrode 87, and has a lead line 85a, which extends in the direction of the axis O, connected thereto. The solid electrolyte substrate 83 is formed from zirconia in which yttria is present in the form of a solid solution as a stabilizing agent, and the porous electrodes 85 and 87 and the lead portions 85a and 87a are formed mainly of Pt.

Additionally, the spacer 93 that forms the measurement gas chamber 91 is constituted mainly of alumina. Additionally, a diffusion rate controlling portion 95, which is arranged parallel to the spacer 93 and allows the hollow measurement gas chamber 91 and the outside to communicate with each other, is formed. The diffusion rate controlling portion 95 is constituted of, for example, porous bodies made of alumina or the like, and serves to control the diffusion rate of an object measurement gas flowing into the measurement gas chamber 91.

Moreover, in the oxygen pump cell 89, an insulating substrate 97 mainly containing alumina is laminated so as to sandwich the porous electrode 85, and the insulating substrate 97 is formed with a ventilation portion 99 constituted by porous bodies. The ventilation portion 99 is used in order to pass oxygen that is moved by the driving of the oxygen pump cell 89 therethrough.

In addition, the measurement gas chamber 91 is formed so as to be located on the front end side of the element portion 71. A portion, which is formed by the measurement gas chamber 91, the porous electrodes 77 and 79 of the oxygen concentration cell 81, the region of the solid electrolyte substrate 75 sandwiched by the electrodes 77 and 79, the porous electrodes 85 and 87 of the oxygen pump cell 89, the region of the solid electrolyte substrate 83 sandwiched by the electrodes 85 and 87, and the like, is equivalent to the detecting portion 19.

On the other hand, in the heater 73, a heater element pattern 105 mainly containing Pt is formed so as to be sandwiched between insulating substrates 101 and 103 mainly containing alumina. The heater element pattern 105 is formed from a heating portion 105a provided on the front end side, and two heater lead portions 105b connected to the heating portion 105a.

In such a detecting element 7, three electrode pads 25 to 29 are formed at a rear end portion (right side in FIG. 4) of the first principal surface 21, and two electrode pads 31 and 33 are formed at a rear end portion of the second principal surface 23.

Among these, the electrode pad (right electrode pad of FIG. 3) 29 of the first principal surface 21 is electrically connected to the lead portion 87a connected to the porous electrode 87, via a through hole conductor 104a provided in the insulating substrate 97 and a through hole conductor 106a provided in the solid electrolyte substrate 83. Moreover, the electrode pad 29 is electrically connected to the lead portion 77a connected to the porous electrode 77, via the through hole conductor 104a provided in the insulating substrate 97, the through hole conductor 106a provided in the solid electrolyte substrate 83, and a through hole conductor 108a provided in the spacer 93. That is, the electrode pad is electrically connected in the form in which the porous electrode 77 and the porous electrode 87 are shared.

Additionally, the electrode pad (central electrode pad of FIG. 3) 27 is electrically connected to the lead portion 79a connected to the porous electrode 79, via a through hole conductor 104b provided in the insulating substrate 97, a through hole conductor 106b provided in the solid electrolyte substrate 83, a through hole conductor 108b provided in the spacer 93, and a through hole conductor 110a provided in the solid electrolyte substrate 75. Moreover, the electrode pad (left-hand side electrode pad of FIG. 3) 25 is electrically connected to the lead portion 85a connected to the porous electrode 85, via a through hole conductor 104c provided in the insulating substrate 97.

Moreover, the electrode pads 31 and 33 of the second principal surface 23 are respectively electrically connected to both ends of the heater element pattern 105 (heater lead portion 105b) via through hole conductors 112.

Next, the details of the present embodiment will be described.

Figure 5A:
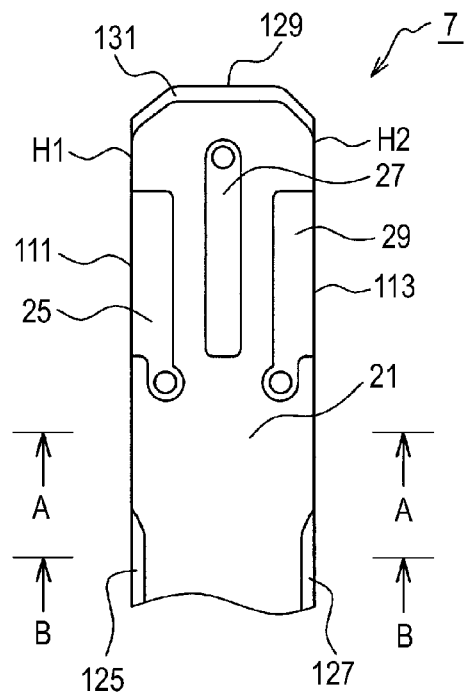
FIG. 5A is a front view showing the rear end portion of the detecting element.
Figure 5B:
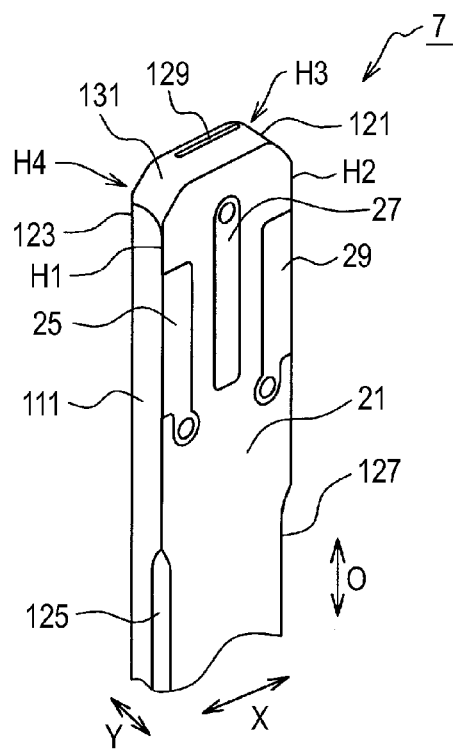
FIG. 5B is a perspective view showing the rear end portion of the detecting element.
Figure 6A:
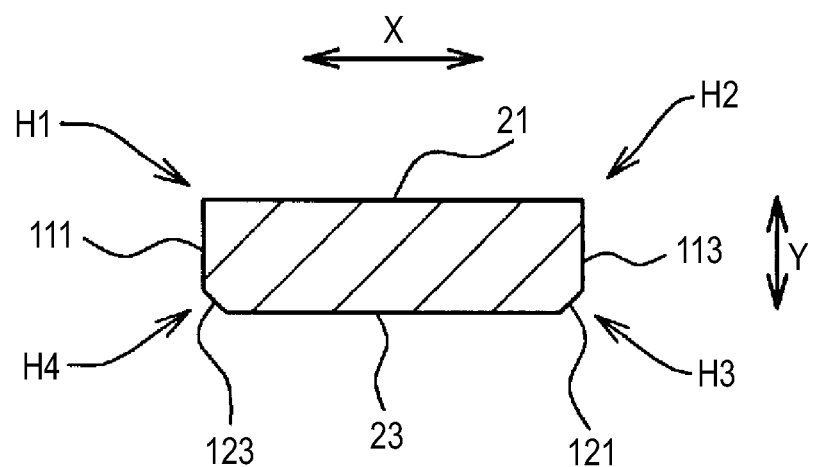
FIG. 6A is a cross-sectional view (in A-A of FIG. 5A) of the detecting element.
Figure 6B:
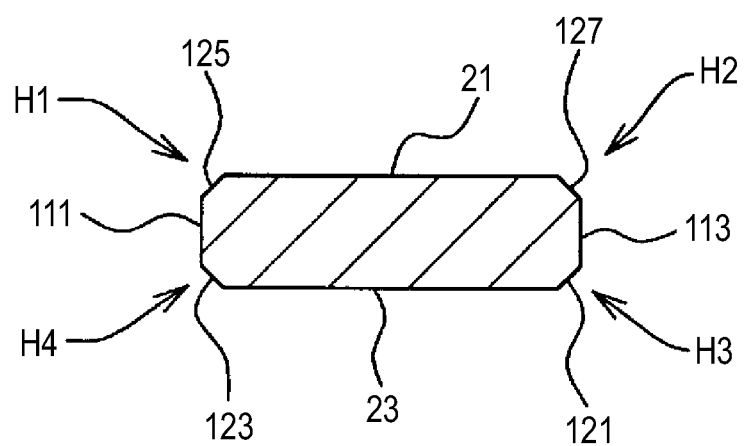
FIG. 6B is a cross-sectional view (in B-B of FIG. 5A) of the detecting element.

Since the detecting element 7 having the above-described configuration is a plate material with a long and substantially rectangular parallelepiped shape, and as shown in FIGS. 5 and 6, includes four sides (axis ridgelines) H1, H2, H3 and H4 that extend along the direction of the axis O.

In detail, the detecting element 7 includes four surfaces of the first principal surface 21 and the second principal surface 23 and a first side surface 111 and a second side surface 113 (connected to both the principal surfaces 21 and 23), in the radial direction perpendicular to the direction of the axis O of the detecting element 7. Additionally, the detecting element 7 includes a first side H1 that is a first axis ridgeline formed by the first principal surface 21 and the first side surface 111, a second side H2 that is a second axis ridgeline formed by the first principal surface 21 and the second side surface 113, a third side H3 that is a third axis ridgeline formed by the second principal surface 23 and the second side surface 113, and a fourth side H4 that is a fourth axis ridgeline formed by the second principal surface 23 and the first side surface 111.

In the present embodiment, C chamfering (for example, C chamfering length 0.1 to 0.3 mm) is performed on the third side H3 and the fourth side H4 on both sides, in the width direction, of the second principal surface 23 side that is the heater 73 side, in the overall detecting element 7 ranging from the front end side to the rear end side, and a third long side chamfered portion 121 and a fourth long side chamfered portion 123 are formed, respectively.

Additionally, C chamfering (for example, C chamfering length 0.1 to 0.3 mm) is performed on the first side H1 and the second side H2 on both sides, in the width direction, of the first principal surface 21 side that is the element portion 71 side, from the front end side of the detecting element 7 to a region before the electrode pads 25 to 29 on the rear end side, and a first long side chamfered portion 125 and a second long side chamfered portion 127 are formed, respectively. That is, C chamfering is not performed on the portions of the first side H1 and the second side H2 outside the electrode pads 25 and 29 in the width direction.

Moreover, in the present embodiment, as shown in FIGS. 7A and 7B, a periphery chamfered portion 131 (for example, periphery chamfering length: 10 mm or less in radius) is formed on the rear end side (upper side in FIG. 7B) of the detecting element 7 by performing periphery chamfering on four ridgelines around a rear end surface 129 so as to leave the rear end surface 129 at the center.

In addition, in the periphery chamfered portion 131, a periphery chamfered portion on the first principal surface 21 side is a first chamfered portion 133, a periphery chamfered portion on the second principal surface 23 side is a third chamfered portion 135, a periphery chamfered portion on the first side surface 111 side is a second chamfered portion 137, and a periphery chamfered portion on the second side surface 113 side is a fourth chamfered portion 139.

Particularly, in the present embodiment, as shown in FIG. 7B, the angle θ1 between a first width ridgeline HR1 formed by the first principal surface 21 and the first chamfered portion 133, and the first side H1 formed by the first side surface 111 and the first principal surface 21 is set to an angle (for example, 95° or more) exceeding 90°. In addition, the angle θ1 is taken as the angle between a tangential line T1 of the first width ridgeline HR1 at a corner portion S1L, and the first side H1.

Moreover, since the appearance shape of the detecting element 7 is bilaterally symmetrical in this drawing, the angle (angle at a corner portion S1R) between the first width ridgeline HR1 and the second side H2 is set similarly to the angle θ1 between the first width ridgeline HR1 and the second side H2. Moreover, a central portion of the first width ridgeline HR1 in the width direction has a circular-arc shape that protrudes to the rear end side.

Additionally, as shown in FIG. 7C, the angle θ2 between a first thickness ridgeline AR1 formed by the first side surface 111 and the second chamfered portion 137, and the first side H1 is set to an angle (for example, 95° or more) exceeding 90°. In addition, the angle θ2 is taken as the angle between a tangential line T2 of the first thickness ridgeline AR1 at a corner portion S2, and the first side H1.

Moreover, since the appearance shape of the detecting element 7 is bilaterally symmetrical in this drawing, also on the second side surface 113 side, the angle between the second thickness ridgeline AR2 (refer to FIG. 7A) and the second side H2 is set similarly to the angle θ2 between the tangential line T2 of first thickness ridgeline AR1 and the second side H2.

Moreover, as shown in FIG. 7C, the (maximum) chamfering length of the first chamfered portion 133 in the direction of the axis is set to be larger than the (maximum) chamfering length of the third chamfered portion 135 in the direction of the axis by Δx (for example, 0.2 mm). In addition, since the appearance shape of the detecting element 7 is bilaterally symmetrical in FIG. 7B, the same difference Δx between the chamfering lengths is set as described above at the left and right ends of this drawing. In addition, although the first chamfered portion 133 varies in the chamfering length in the direction of the axis O in the width direction, the chamfering lengths in the direction of the axis O passing through the corner portion S1L and S1R (or corner portion S2) are compared in this case.

In addition, the total value of the width dimensions of the electrode pads 25 and 29 on the first principal surface 21 side is, for example, 1.6 mm, and the value of the width dimension of the first principal surface 21 is, for example, 4.2 mm, and "the total value of the width dimensions of the respective electrode pads 25 and 29/the value of the width dimension of the first principal surface 21" is 0.38, and is set to 0.4 or less.

b) Next, a method of manufacturing the air-fuel ratio sensor 1 of the present embodiment will be described.

Method of Manufacturing Detecting Element 7

As for the detecting element 7, various laminated materials serving as the material of the detecting element 7, that is, unbaked solid electrolyte sheets serving as the solid electrolyte substrates 75 and 83 of the element portion 71, an unbaked insulating sheet serving as the insulating substrates 97, 101 and 103 of the heater 73 or the like, and the like are brought into a laminated state to obtain a non-compressed laminate.

In addition, the porous electrodes 77, 79, 85 and 87, the lead portions 77a, 79a, 85a and 87a, the through hole conductors 104a, 104b, 104c, 106a, 106b, 108a, 108b and 110a, unbaked electrode pads serving as the electrode pads 25 to 33, and the like are formed on the non-compressed laminate by methods well known to those of ordinary skill in this field of art.

Among these, for example, as for the production of the unbaked solid electrolyte sheets, alumina powder, butyral resin, or the like is added to ceramic powder mainly containing zirconia, and a mixed solvent (toluene and methylethylketone) is further mixed therein to generate a slurry. Then, this slurry is formed into a sheet using a doctor blade, and the mixed solvent is volatilized to produce the unbaked solid electrolyte sheets.

Additionally, as for the production of the unbaked insulating sheet, butyral resin and dibutylphthalate are added to a ceramic powder mainly containing alumina, and a mixed solvent (toluene and methylethylketone) is further mixed therein to generate a slurry. Then, this slurry is formed into a sheet using a doctor blade, and the mixed solvent is volatilized to produce the unbaked solid electrolyte sheets.

Then, a compressed compact is obtained by pressing this non-compressed laminate with an applied pressure of 1 MPa. In addition, since the manufacturing method of obtaining the non-compressed laminate (before pressing) is the same as that of a general manufacturing method of the detecting element, a detailed description thereof is omitted.

Then, a plurality of (for example, ten) unbaked laminates that approximately coincide with the size of the detecting element 7 is obtained by cutting a compact obtained by pressing, with a predetermined size.

Thereafter, resin is eliminated from this unbaked laminate, and main baking is performed at a baking temperature of 1500° C. for 1 hour to obtain a laminate after baking.

Additionally, the detecting element 7 in which the porous layer 17 is formed is obtained by forming an unbaked porous portion (serving as the porous layer 17) around the front end side of the laminate after baking, and heat-treating the laminate after baking in which the unbaked porous portion is formed.

Chamfering Method of Detecting Element 7

First, long side chamfering is performed on the baked detecting element 7.

Specifically, although not shown, four sides (first to fourth sides H1 to H4) of the detecting element 7 that extend in the longitudinal direction abut a rotating grindstone to perform the well-known C chamfering.

In addition, although chamfering is performed all from the front end of the detecting element 7 to the rear end thereof on the third side H3 and the fourth side H4 in the width direction on the second principal surface 23 side, chamfering is performed from the front end of the detecting element 7 to only the near side of the electrode pads 25 to 29, on the first side H1 and the second side H2 in the width direction of the first principal surface 21.

Next, in the present embodiment, the rear end portion of the detecting element 7 is rotated about the axis O of the detecting element 7 in a state where the rear end portion is applied to the rotating grindstone by adding weight (that is, the weighting control of adding a predetermined weight is performed), and periphery chamfering of the whole circumference of the rear end surface 129 is performed. Thereby, the periphery chamfered portion 131 that surrounds the periphery of the rear end surface 129 is formed.

Sensor Assembly Process

Thereafter, the assembly process of assembling the detecting element 7 to the metal shell 5 is performed.

That is, in this process, the detecting element 7 produced by the above manufacturing method is inserted into the metal holder 51, the detecting element 7 is further fixed using the ceramic holder 41 and the talc ring 43, thereby producing an assembly. Thereafter, this assembly is fixed to the metal shell 5, the rear end portion side of the detecting element 7 in the direction of the axis is inserted through the talc ring 45 and the ceramic sleeve 9, and these are inserted into the metal shell 5.

Then, the ceramic sleeve 9 is crimped to the rear end portion 47 of the metal shell 5 to produce a lower assembly. In addition, the protector 55 is attached to the lower assembly in advance.

On the other hand, the external cylinder 57, the separator 13, the grommet 61, and the like are assembled by a well-known method to produce an upper assembly. Then, the lower assembly and the upper assembly are joined by a well-known method to obtain the air-fuel ratio sensor 1.

c) Next, the effects of the present embodiment will be described.

In the present embodiment, the angle θ1 between the first width ridgeline HR1 formed by the first principal surface 21 and the first chamfered portion 133, and the first side H1 formed by the first side surface 111 and the first principal surface 21 is set to be larger than 90°. Thereby, the first width ridgeline HR1 is provided closer to the rear end side than the corner portion S1L. Hence, when the rear end portion of the detecting element 7 is inserted into the through hole 11 of the separator 13, even if the detecting element 7 is inserted at an incline with respect to the separator 13 and not coaxially with the separator 13, the opening or inner surface (inner surface of the through hole 11) of the separator 13 comes into contact with the first width ridgeline HR1. Thereby, the corner portion S1L of the detecting element 7 does not easily come into contact with the opening or inner surface of the separator 13. As a result, chipping can be avoided.

Moreover, the corner portion S1L becomes smoother by setting the angle θ1 between the first side H1 and the first width ridgeline HR1 so as to be larger than 90°. As a result, even if the detecting element 7 is inserted at an incline with respect to the separator 13 and not coaxially with the separator 13, and the corner portion S1L of the detecting element 7 strikes the opening or inner surface of the separator 13, chipping does not easily occur.

Moreover, since the first chamfered portion 133 is provided between the first principal surface 21 and the rear end surface 129, when the rear end portion of the detecting element 7 is inserted into the separator 13, the first chamfered portion 133 is easily inserted to follow the through hole 11 of the separator 13.

Similarly, since the detecting element 7 is bilaterally symmetrical in FIG. 7B, the first width ridgeline HR1 is provided closer to the rear end side than the corner portion S1R where the second side H2 and the first width ridgeline HR1 are combined, by setting the angle θ1 (the same sign is used since it is symmetrical) between the first width ridgeline HR1 and the second side H2 to be larger than 90°. Thereby, when the rear end portion of the detecting element 7 is inserted into the separator 13, even if the detecting element 7 is inserted at an incline with respect to the separator 13 and not coaxially with the separator 13, the opening or inner surface of the separator 13 comes into contact with the first width ridgeline HR1. Thereby, the corner portion S1R of the detecting element 7 does not easily come into contact with the opening or inner surface of the separator 13. As a result, chipping can be avoided.

Moreover, the corner portion S1R where the second side H2 and the first width ridgeline HR1 are combined becomes smoother by setting the angle θ1 between the first width ridgeline HR1 and the second side H2 to be larger than 90°. As a result, even if the detecting element 7 is inserted at an incline with respect to the separator 13 and not coaxially with the separator 13, and the corner portion S1R of the detecting element 7 strikes the opening or inner surface of the separator 13, chipping does not easily occur.

Moreover, the central portion of the first width ridgeline HR1 in the width direction has a circular-arc shape that protrudes to the rear end side. Thereby, when the rear end portion of the detecting element 7 is inserted into the separator 13, the central portion of the detecting element 7 abuts in a case where the inner surface of the separator 13 comes into contact with the first width ridgeline HR1. As a result, the corner portion S1L or S1R of the detecting element 7 does not easily come into contact with the opening or inner surface of the separator 13, and consequently, chipping can be avoided.

Additionally, the angle θ2 between the first thickness ridgeline AR1 formed by the first side surface 111 and the second chamfered portion 137, and the first side H1 is set to be larger than 90°. Thereby, the first thickness ridgeline AR1 is provided closer to the rear end side than the corner portion S2. In addition, since the detecting element 7 is bilaterally symmetrical in FIG. 7B and the angle between (i) the second thickness ridgeline AR2 on the second side surface 113 side and (ii) the second side H2 is also the same, a description thereof is omitted. Hence, when the detecting element 7 is inserted into the separator 13, even if the detecting element 7 is inserted at an incline with respect to the separator 13 and not coaxially with the separator 13, the opening or inner surface of the separator 13 comes into contact with the first thickness ridgeline AR1. Thereby, the corner portion S2 of the detecting element 7 does not easily come into contact with the opening or inner surface of the separator 13. As a result, chipping can be avoided.

Moreover, the corner portion S2 becomes smoother by setting the angle between the first side H1 and the first thickness ridgeline AR1 so as to be larger than 90°. As a result, when the rear end portion of the detecting element 7 is inserted into the separator 13, even if the detecting element 7 is inserted at an incline with respect to the separator 13 and not coaxially with the separator 13, and the corner portion S2 of the detecting element 7 strikes the opening or inner surface of the separator 13, chipping does not easily occur.

Moreover, since the second chamfered portion 137 is provided between the first side surface 111 and the rear end surface 129, when the rear end portion of the detecting element 7 is inserted into the separator 13, the second chamfered portion 137 is easily inserted to follow the through hole 11 of the separator 13.

Moreover, in the present embodiment, the (maximum) chamfering length of the first chamfered portion 133 in the direction of the axis is set to be larger than the (maximum) chamfering length of the third chamfered portion 135 in the direction of the axis. Thereby, even if the first long side chamfered portion 125 or the second long side chamfered portion 127 is not connected to the first chamfered portion 133, chipping does not easily occur in the corner portion S1 because the corner portion S1 becomes smooth.

Moreover, in the present embodiment, the two electrode pads 25 and 29 are provided side by side in the width direction on the first principal surface 21 of the detecting element 7 so as to be adjacent to the first side H1 and the second side H2. Further, the ratio of the total value of the width dimensions of the electrode pads 25 and 29 on the first principal surface 21 side and the value of the width dimension of the first principal surface 21 (the total value of the width dimensions of the respective electrode pads 25 and 29/the value of the width dimension of the first principal surface 21) is 0.4 or less.

In a case where the width dimension of the electrode pads 25 and 29 is small in this way, it is dimensionally difficult to perform chamfering all from the front end side to the rear end side thereof on the respective sides H1 and H2 of the detecting element 7 in the direction of the axis O (so as to run along the outer sides of the electrode pads 25 and 29). Therefore, chipping can be suppressed even if chamfering is not performed along the outer sides of the electrode pads 25 and 29 like in the present embodiment by providing the first chamfered portion 133 at the rear end portion of the detecting element 7.

Second Embodiment

Next, although a second embodiment will be described, the description of the same content as the first embodiment is omitted.

Since the present embodiment is different from the first embodiment only in the configuration of the detecting element, the detecting element will be described.

As shown in FIGS. 8A and 8B, for a detecting element 201 to be used for the air-fuel ratio sensor of the present embodiment, similarly to the first embodiment, three electrode pads 205, 207 and 209 are formed on the rear end side of a first principal surface 203 (that is on the element portion side).

The detecting element 201 of the second embodiment, as shown in FIGS. 8A and 8B, includes four sides (axis ridgelines) H1, H2, H3 and H4 that extend along the direction of the axis O. In detail, the detecting element 201 includes four surfaces of the first principal surface 203 and the second principal surface 215 and a first side surface 210 and a second side surface 212 (connected to both the principal surfaces 203 and 215), in the radial direction perpendicular to the direction of the axis O of the detecting element 201. Additionally, the detecting element 201 includes the first side H1 that is an axis ridgeline formed by the first principal surface 203 and the first side surface 210, the second side H2 that is an axis ridgeline formed by the first principal surface 203 and the second side surface 212, the third side H3 that is an axis ridgeline formed by the second principal surface 215 and the second side surface 212, and a fourth side H4 that is an axis ridgeline formed by the second principal surface 215 and the first side surface 210.

Additionally, a third long side chamfered portion 217 and a fourth long side chamfered portion 219 are respectively formed on the third side H3 and the fourth side H4 on both sides, in the width direction, of the second principal surface 215 (that is the heater side) of the detecting element 201 by C chamfering so as to range from the front end of the detecting element 201 to the rear end thereof along the direction of the axis.

Moreover, in the second embodiment, a first long side chamfered portion 221 and a second long side chamfered portion 223 are respectively formed on the first side H1 and the second side H2 on both sides, in the width direction, of the first principal surface 203 of the detecting element 201 by C chamfering so as to range from the front end of the detecting element 201 to the rear end thereof along the direction of the axis.

Additionally, similarly to the first embodiment, periphery chamfering is performed over the whole circumference of a rear end surface 211, and a periphery chamfered portion 213 is formed on the rear end side of the detecting element 201. In addition, in the periphery chamfered portion 213, a periphery chamfered portion on the first principal surface 203 side is a first chamfered portion 233, a periphery chamfered portion on the second principal surface 215 side is a third chamfered portion 235, a periphery chamfered portion on the first side surface 210 side is a second chamfered portion 237, and a periphery chamfered portion on the second side surface 212 side is a fourth chamfered portion 239.

In the second embodiment, as shown in FIG. 8B, the angle θ1 between a first width ridgeline HR1 that is formed by the first principal surface 203 and the first chamfered portion 233, and the first long side chamfered portion 221 (more specifically, an axis ridgeline that is formed by the first long side chamfered portion 221 and the first principal surface 203) is set to an angle (for example, 95° or more) exceeding 90°.

Moreover, since the appearance shape of the detecting element 7 is bilaterally symmetrical in this drawing, the angle between the first width ridgeline HR1 and the second long side chamfered portion 223 (more specifically, an axis ridgeline that is formed by the second long side chamfered portion 223 and the first principal surface 203) is also set similarly to the angle θ1 between the first width ridgeline HR1 and the first long side chamfered portion 221. Moreover, a central portion of the first width ridgeline HR1 in the width direction has a circular-arc shape that protrudes to the rear end side.

Additionally, the angle θ2 between a first thickness ridgeline AR1 formed by the first side surface 210 and the second chamfered portion 237, and the first long side chamfered portion 221 (more specifically, an axis ridgeline that is formed by the first long side chamfered portion 221 and the first side surface 210) is set to an angle (for example, 95° or more) exceeding 90°. In addition, since the appearance shape of the detecting element 7 is bilaterally symmetrical in this drawing, the angle between the second thickness ridgeline (not shown) and the second long side chamfered portion 223 is set similarly to the angle θ2 also on the second side surface 212 side.

The same effects as the first embodiment are also exhibited by the present embodiment.

Third Embodiment

Next, although a third embodiment will be described, the description of the same contents as the first embodiment is omitted.

Since the present embodiment is different from the first embodiment only in the configuration of the detecting element, the detecting element will be described.

Figure 9A:
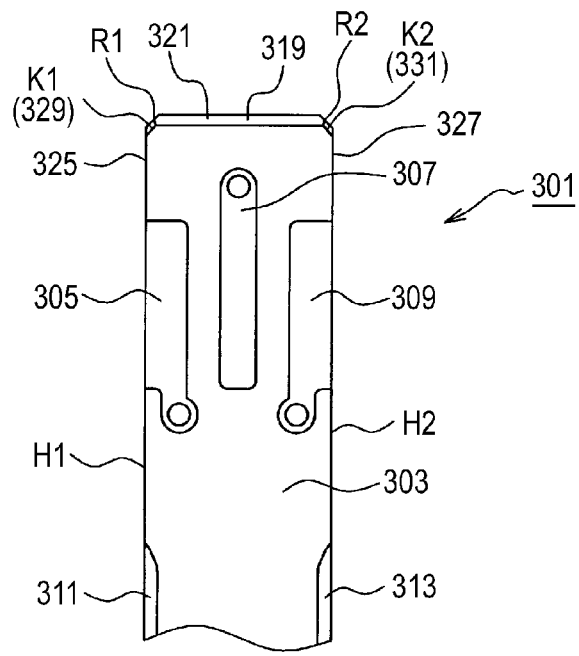
FIG. 9A is a front view showing a rear end portion of a detecting element of a third embodiment.
Figure 9B:
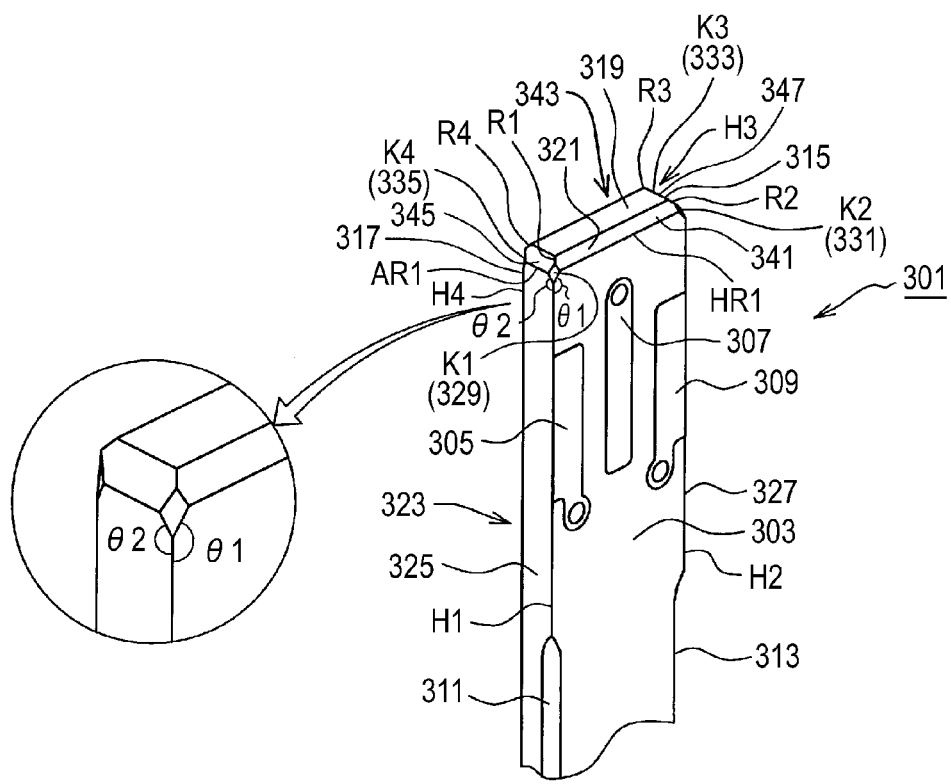
FIG. 9B is a perspective view showing the rear end portion of the detecting element.

As shown in FIGS. 9A and 9B, for a detecting element 301 to be used for the air-fuel ratio sensor of the present embodiment, similarly to the first embodiment, three electrode pads 305, 307 and 309 are formed on the rear end side of a first principal surface 303 (that is on the element portion side).

The detecting element 301 of the third embodiment, as shown in FIGS. 9A and 9B, includes four sides (axis ridgelines) H1, H2, H3 and H4 that extend along the direction of the axis O. In detail, the detecting element 301 includes four surfaces of the first principal surface 303 and a second principal surface 323 and a first side surface 325 and a second side surface 327 (connected to both the principal surfaces 303 and 323), in the radial direction perpendicular to the direction of the axis O of the detecting element 301. Additionally, the detecting element 301 includes the first side H1 that is an axis ridgeline formed by the first principal surface 303 and the first side surface 325, the second side H2 that is an axis ridgeline formed by the first principal surface 303 and the second side surface 327, the third side H3 that is an axis ridgeline formed by the second principal surface 323 and the second side surface 327, and a fourth side H4 that is an axis ridgeline formed by the second principal surface 323 and the first side surface 325.

Additionally, the first to fourth long side chamfered portions 311, 313, 315 and 317 C-chamfered similarly to the first embodiment are formed at the first to fourth sides H1 to H4 of the outer periphery of the detecting element 301.

Moreover, C chamfering is performed over the whole circumference of a rear end surface 319, and a C chamfered portion 321 is formed on the rear end side of the detecting element 301.

The C chamfered portion 321 is formed by performing C chamfering by a predetermined C chamfering length, parallel to the first principal surface 303, the second principal surface 323, the first side surface 325, and the second side surface 327 similar to the related art. In addition, in the C chamfered portion 321, a C chamfered portion on the first principal surface 303 side is a first chamfered portion 341, a C chamfered portion on the second principal surface 323 side is a third chamfered portion 343, a C chamfered portion on the first side surface 325 side is a second chamfered portion 345, and a C chamfered portion on the second side surface 327 side is a fourth chamfered portion 347.

Moreover, in the present embodiment, rhomboidal corner C chamfered portions 329, 331, 333 and 335 are formed in the C chamfered portion 321 by further performing C chamfering so that points K1 to K4 where respective ridgelines R1, R2, R3 and R4 ranging from the rear end surface 319 to the first to fourth sides H1 to H4 intersect the rear ends of the first to fourth sides H1 to H4 are flattened.

In detail, a corner C chamfered portion 329 (K1) is provided so as to be surrounded by the first chamfered portion 341, the second chamfered portion 345, the first principal surface 303 and the first side surface 325; a corner C chamfered portion 331 (K2) is provided so as to be surrounded by the first chamfered portion 341, the fourth chamfered portion 347, the first principal surface 303 and the second side surface 327; a corner C chamfered portion 333 (K3) is provided so as to be surrounded by the third chamfered portion 343, the fourth chamfered portion 347, the second principal surface 323 and the second side surface 327; and a corner C chamfered portion 335 (K4) is provided so as to be surrounded by the third chamfered portion 343, the second chamfered portion 345, the second principal surface 323 and the first side surface 325.

In addition, the inclination angles of the corner C chamfered portions 329 to 335 to the direction of the axis are set to be smaller than the inclination angles of the respective ridgelines R1 to R4.

In the third embodiment, as shown in FIG. 9B, the angle θ1 between (i) a first width ridgeline HR1 formed by the first main surface 303 and the first chamfered portion 341 and (ii) the first side H1 is set to an angle (for example, 95° or more) exceeding 90°. In addition, in the third embodiment, since the corner C chamfered portion 329 is provided, a straight line of the first width ridgeline HR1 is bent in the middle in the width direction. In this case, the angle between the portion of the first width ridgeline HR1 corresponding to the corner C chamfered portion 329 and the first side H1 is taken as the angle θ1.

Moreover, since the appearance shape of the detecting element 7 is bilaterally symmetrical in this drawing, the angle between the first width ridgeline HR1 (in detail, the portion of the first width ridgeline HR1 corresponding to the corner C chamfered portion 331), and the second side H2 is also set similarly to the angle θ1.

Additionally, the angle θ2 between (i) a first thickness ridgeline AR1 formed by the first side surface 325 and the second chamfered portion 345 and (ii) the first side is set to an angle (for example, 95° or more) exceeding 90°. In addition, in the third embodiment, since the corner C chamfered portion 329 is provided, a straight line of the first thickness ridgeline AR1 is bent in the middle in the width direction. In this case, the angle between the portion of the first thickness ridgeline AR1 corresponding to the corner C chamfered portion 329 and the first side H1 is taken as the angle θ2.

Additionally, since the appearance shape of the detecting element 7 is bilaterally symmetrical in this drawing, the angle between the second thickness ridgeline (not shown) and the second side H2 is set similarly to the angle θ2 also on the second side surface 327 side.

Since the same effects as the first embodiment are also exhibited by the present embodiment and not periphery chamfering but C chamfering is performed, there is an additional advantage that processing is easy.

Fourth Embodiment

Next, although a fourth embodiment will be described, the description of the same contents as the third embodiment is omitted.

Since the present embodiment is different from the third embodiment only in the configuration of the detecting element (particularly, a corner C chamfered portion), the detecting element will be described.

Figure 10A:
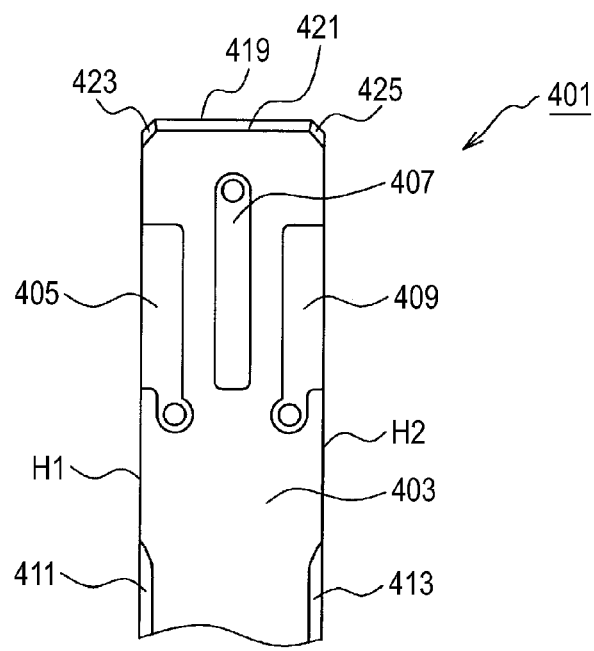
FIG. 10A is a front view showing a rear end portion of a detecting element of a fourth embodiment.
Figure 10B:
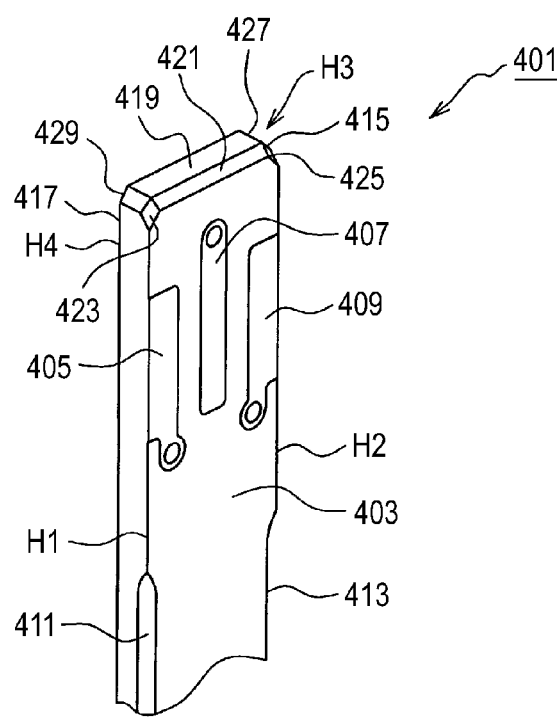
FIG. 10B is a perspective view showing the rear end portion of the detecting element.
Figure 11A:
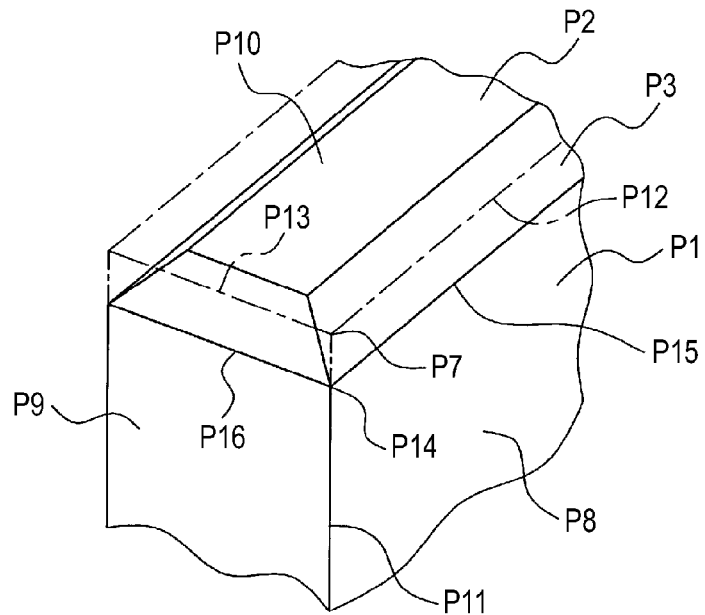
FIGS. 11A and 11B are explanatory views of the related art.
Figure 11B:
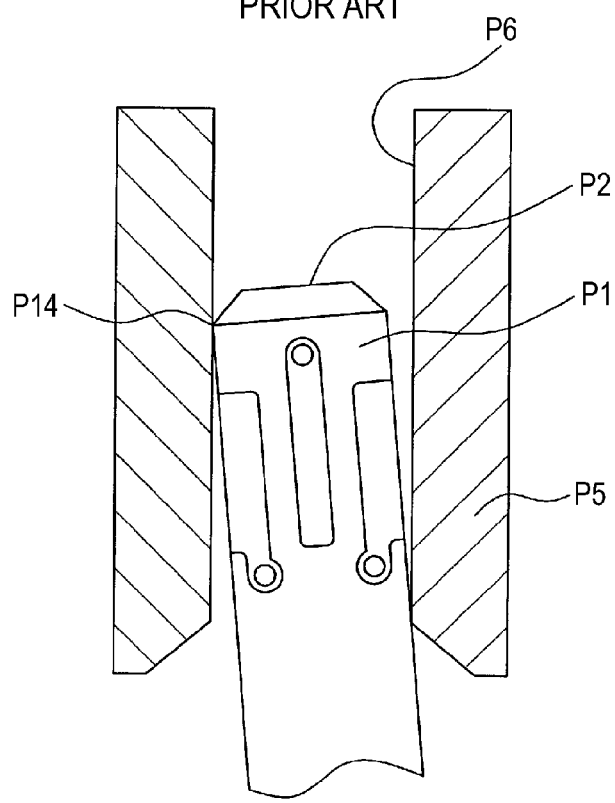

As shown in FIGS. 10A and 10B, as for a detecting element 401 to be used for the air-fuel ratio sensor of the present embodiment, similarly to the third embodiment, three electrode pads 405, 407 and 409 are formed on the rear end side of a first principal surface 403 (that is on the element portion side).

Additionally, first to fourth long side chamfered portions 411, 413, 415 and 417 C-chamfered similarly to the third embodiment are formed at first to fourth sides H1 to H4 of the outer periphery of the detecting element 401.

Moreover, C chamfering is performed over the whole circumference of a rear end surface 419, and a C chamfered portion 421 is formed on the rear end side of the detecting element 401.

In the present embodiment, particularly in the C chamfered portion 421, C chamfering is performed within a range from four corners of the rear end surface 419 to the rear ends (upper ends in this drawing) of the first to fourth sides H1 to H4, and rhomboidal corner C chamfered portions 423, 425, 427 and 429 (longer in the longitudinal direction than the third embodiment) are formed.

The same effects as the third embodiment are also exhibited by the present embodiment.

Although the embodiments of the invention have been described hitherto, the invention is not limited to the above embodiments, and the invention can be carried out in various aspects without departing from the spirit and scope of the claims appended hereto.

For example, in the present embodiment, the periphery chamfered portion 133, 213 or the C chamfered portion 321, 421 is formed over the whole circumference of the rear end side of the detecting element 7, 201, 301 or 401. However, the invention is not limited thereto, and it is only necessary to provide the first chamfered portion at least between the first principal surface and the rear end surface. In addition, in the present embodiment, for convenience of description, the surfaces on which the electrode pads are provided are the first principal surface and the second principal surface, and the surfaces adjacent to the first principal surface and the second principal surface are the first side surface and the second side surface. However, surfaces on which the electrode pads are not provided may be the first principal surface and the second principal surface, and surfaces adjacent to the first principal surface and the second principal surface are the first side surface and the second side surface.

This application is based on Japanese Patent Application No. 2011-211327 filed Sep. 27, 2011 and Japanese Patent Application No. 2012-178373 filed Aug. 10, 2012, the disclosures of which are incorporated herein by reference in their entirety.

What is claimed is:

1. A gas sensor comprising:
   a plate-shaped detecting element that extends in the direction of an axis and has a front end portion directed at an object measurement gas;
   a metal shell surrounding a periphery of the detecting element such that the front end portion and a rear end portion of the detecting element protrude therefrom; and
   a tubular member that accommodates the rear end portion of the detecting element,
   wherein the detecting element has a pair of principal surfaces and a pair of side surfaces which are adjacent to the pair of principal surfaces in a radial direction perpendicular to the direction of the axis,
   wherein a first chamfered portion is provided between at least a first principal surface of the pair of principal surfaces and a rear end surface of the detecting element,
   wherein an angle between a first axis ridgeline portion formed by the first principal surface and a first side surface that is one of the pair of side surfaces and extending in the direction of the axis, and a first width ridgeline formed by the first principal surface and the first chamfered portion and extending in a width direction is larger than 90° and less than 180°,
   wherein a plurality of electrode pads extending in the direction of the axis is provided on the first principal surface at the rear end portion of the detecting element,
   at least one of the plurality of electrode pads is disposed adjacent to a portion of the first axis ridgeline portion, and
   a first long side chamfered portion is provided extending between said first principal surface and said first side surface in the radial direction and extends in the direction of the axis, such that said first long side chamfered portion does not exist on the portion of the first axis ridgeline portion that is adjacent to the least one of the plurality of electrode pads and a length of the first long side chamfered portion is less than a length of the first axis ridgeline portion in the direction of the axis.

2. The gas sensor as claimed in claim 1,
wherein the angle between a second axis ridgeline portion formed by the first principal surface and a second side surface different from the first side surface of the pair of side surfaces and extending in the direction of the axis, and the first width ridgeline is larger than 90° and less than 180°.

3. The gas sensor as claimed in claim 2,
wherein the first width ridgeline has a circular-arc shape in which a central portion thereof in the width direction protrudes to a rear end side.

4. The gas sensor as claimed in claim 1,
wherein a second chamfered portion is provided between the first side surface and the rear end surface, and
wherein the angle between a first thickness ridgeline formed by the first side surface and the second chamfered portion and extending in the thickness direction of the detecting element, and the first axis ridgeline portion is larger than 90° and less than 180°.

5. The gas sensor as claimed in claim 1, further comprising:
a second axis ridgeline portion formed by the first principal surface and a second side surface different from the first side surface of the pair of side surfaces and extending in the direction of the axis,
wherein two electrode pads among the plurality of electrode pads are provided side by side along the width direction on the first principal surface of the detecting element so as to be adjacent to the first axis ridgeline portion and the second axis ridgeline portion, and
wherein a value obtained by dividing a total value of the width dimensions of the two electrode pads by the width dimension of the first principal surface is 0.4 or less.

6. The gas sensor as claimed in claim 1,
wherein a third chamfered portion is provided between a second principal surface different from the first principal surface of the pair of principal surfaces, and the rear end surface of the detecting element, and the long side chamfered portion is provided by the second principal surface and the first side surface so as to be connected to the third chamfered portion, and
wherein a chamfering length in the direction of the axis of the first chamfered portion is larger than the chamfering length in the direction of the axis of the third chamfered portion.

* * * * *